(12) United States Patent
Blundell (10) Patent No.: US 9,116,081 B2
(45) Date of Patent: Aug. 25, 2015

(54) OIL SAMPLE TAP FOR ELECTRICAL EQUIPMENT

(75) Inventor: Heath Blundell, Bakersfield, CA (US)

(73) Assignee: Sunbelt Transformer, Ltd., Temple, TX (US)

( * ) Notice: Subject to any disclaimer, the term of this patent is extended or adjusted under 35 U.S.C. 154(b) by 667 days.

(21) Appl. No.: 13/115,522

(22) Filed: May 25, 2011

(65) Prior Publication Data

US 2012/0297901 A1 Nov. 29, 2012

(51) Int. Cl.
*G01N 1/20* (2006.01)
*H01F 27/14* (2006.01)

(52) U.S. Cl.
CPC . *G01N 1/20* (2013.01); *H01F 27/14* (2013.01)

(58) Field of Classification Search
CPC ......... G01N 1/00; G01N 1/28; G01N 1/2247; H01L 2924/0002; Y10T 436/2575; H01F 27/14
USPC ........... 73/386, 1.72, 863.71, 863.81, 863.83, 73/863.86, 431, 864.34, 863; 361/807; 336/90
See application file for complete search history.

(56) References Cited

U.S. PATENT DOCUMENTS

| | | | | |
|---|---|---|---|---|
| 2,784,563 | A * | 3/1957 | Baker | 62/138 |
| 4,015,479 | A * | 4/1977 | Apple | 73/863.24 |
| 4,035,818 | A * | 7/1977 | King | 396/625 |
| 4,112,737 | A | 9/1978 | Morgan | |
| 4,350,052 | A | 9/1982 | Kendall | |
| 4,763,514 | A * | 8/1988 | Naito et al. | 73/19.11 |
| 5,131,283 | A | 7/1992 | Canfield | |
| 5,258,310 | A | 11/1993 | Abe et al. | |
| 5,299,464 | A | 4/1994 | Bennett | |
| 5,749,942 | A * | 5/1998 | Mattis et al. | 95/46 |
| 5,783,739 | A * | 7/1998 | Miller | 73/12.04 |
| 5,907,110 | A | 5/1999 | Garcia et al. | |
| 5,929,348 | A * | 7/1999 | Stein et al. | 73/865.3 |
| 6,037,592 | A | 3/2000 | Sunshine et al. | |
| 6,256,601 | B1 * | 7/2001 | Wipasuramonton et al. | 703/8 |
| 6,293,163 | B1 | 9/2001 | Johnston et al. | |
| 6,308,748 | B1 | 10/2001 | Nickens et al. | |
| 6,391,096 | B1 * | 5/2002 | Waters et al. | 96/6 |
| 6,522,998 | B1 * | 2/2003 | Mazur et al. | 703/8 |
| 6,718,222 | B2 * | 4/2004 | Bergo et al. | 700/117 |
| 6,968,728 | B2 * | 11/2005 | Gilbert et al. | 73/19.12 |
| 7,247,059 | B2 * | 7/2007 | Greaves | 439/709 |
| 8,099,253 | B1 * | 1/2012 | Rau | 702/113 |
| 8,196,447 | B2 * | 6/2012 | Chen et al. | 73/12.04 |
| 8,364,435 | B2 * | 1/2013 | Battenberg | 702/113 |
| 8,442,775 | B2 * | 5/2013 | Santos | 702/24 |
| 2002/0083781 | A1 * | 7/2002 | Golner et al. | 73/863.83 |
| 2002/0121144 | A1 * | 9/2002 | Stein et al. | 73/862 |
| 2003/0160602 | A1 * | 8/2003 | Anand et al. | 324/126 |
| 2008/0163669 | A1 * | 7/2008 | Gregory et al. | 73/19.02 |
| 2010/0186480 | A1 * | 7/2010 | Cunningham et al. | 73/23.2 |

\* cited by examiner

*Primary Examiner* — Peter Macchiarolo
*Assistant Examiner* — Mohammed Keramet-Amircola
(74) *Attorney, Agent, or Firm* — George M. Tompkins; Tompkins, P.C.

(57) ABSTRACT

An improved electrical equipment housing which includes an oil sample valve and a gas port assembly which are contained within the electrical equipment housing, yet are separated from electrical contacts and may be accessed without exposure to the electrical contacts.

6 Claims, 8 Drawing Sheets

OIL SAMPLE TAP FOR ELECTRICAL EQUIPMENT

TECHNICAL FIELD OF THE INVENTION

The present invention is generally directed towards an apparatus to allow a user to safely obtain a fluid sample from oil-filled electrical equipment.

BACKGROUND ART OF THE INVENTION

Large industrial electrical equipment, such as oil-filled pad mounted transformers, load tap changers, and the like, contain contacts and other parts which can wear out over time. Since these parts are located inside an oil-filled tank, it is very difficult to visually inspect them. Instead, dissolved gas analysis is often used to measure the level of "fault gases" in the oil. The level of fault gases may be used to estimate the condition of the equipment. However, dissolved gas analysis requires an oil sample to be taken from the transformer tank. Typically, the oil sample would be taken from a valve located on the tank within the transformer cabinet. Because the valve is inside the cabinet, alongside exposed electrical contacts, the transformer would need to be de-energized before the sample was taken to avoid the risk of injury or death to the person taking the sample. De-energizing a transformer is costly. What is needed is an apparatus that will allow a user to safely obtain an oil sample from electrical equipment without having to de-energize the equipment. The apparatus is preferably also tamper resistant.

SUMMARY

Problems with prior art oil sampling are solved by providing an improved electrical equipment housing which includes an oil sample valve and a gas port assembly which are contained within the electrical equipment housing, and are separated from electrical contacts and may be accessed without exposure to the electrical contacts. The improved electrical equipment housing preferably comprises: a tank containing electrical equipment and a liquid; electrical contacts extending through a wall of the tank; a liquid sample port; an enclosure surrounding the electrical contacts and the liquid sample port; a cavity containing the liquid sample port, wherein the cavity is configured to substantially physically isolate the liquid sample port from the electrical contacts; and an opening in the enclosure configured to provide access to the cavity while maintaining substantial physical isolation of the liquid sample port from the electrical contacts.

In one embodiment, the electrical equipment housing further comprises a lockable cover configured to selectively close the opening.

In another embodiment, the electrical equipment housing further comprises a second opening, the second opening allowing access to the electrical contacts.

In another embodiment, the electrical equipment housing further comprises a gas and a remote gas port contained in the cavity.

Also provided is a remote sample kit for an electrical equipment housing comprising: a drain connector configured to connect to a drain valve of a tank; a remote sample port; a sample line connecting the drain connector to the remote sample port; and a remote housing containing the remote sample port and configured to attach to a wall of the electrical equipment housing.

In another embodiment, the remote sample kit further comprises: a remote gas port; a gas connector configured to connect to a gas port of the tank; and a gas line connecting the remote gas port to the gas connector.

In another embodiment, the remote housing also contains the remote gas port.

In another embodiment, the remote sample kit further comprises an opening in the remote housing to allow access to the remote sample port through the wall of the electrical equipment housing.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which.

DETAILED DESCRIPTION OF THE PREFERRED EMBODIMENT

Figure 1:
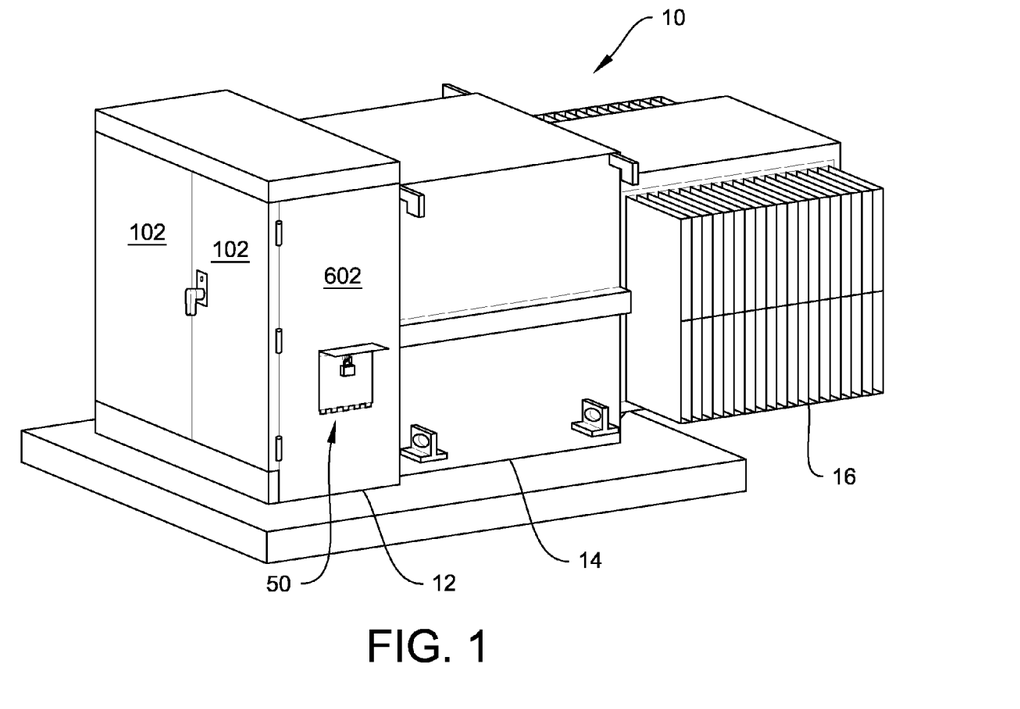
FIG. 1 is a perspective view of a pad-mounted transformer with an embodiment of the present invention.
Figure 2A:
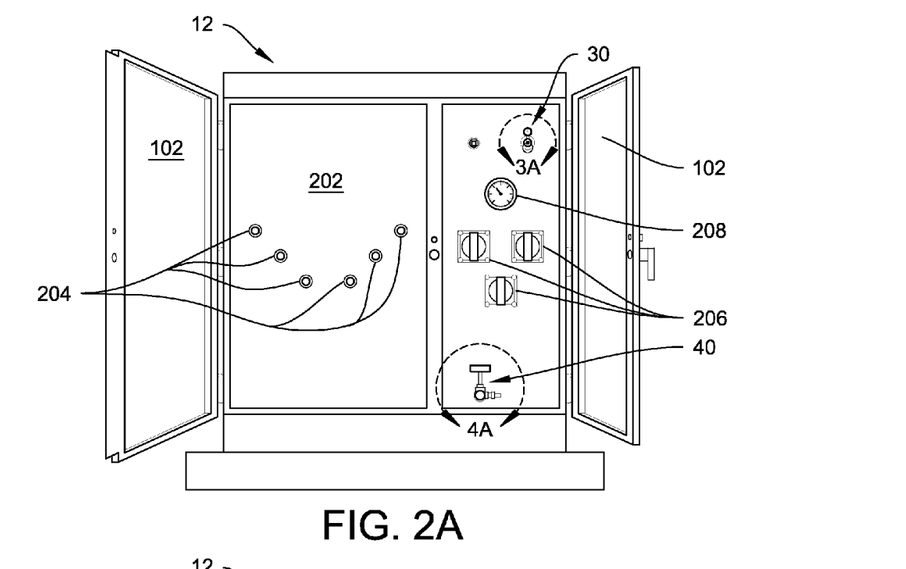
FIG. 2A is a view of a typical transformer cabinet.
Figure 2B:
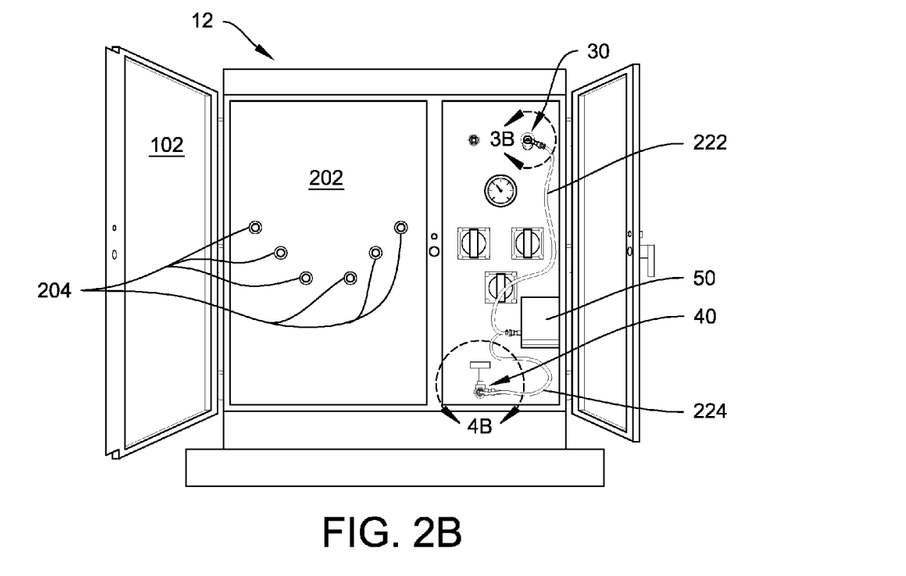
FIG. 2B is a view of a typical transformer cabinet including an embodiment of the present invention.

Referring to FIG. 1, reference number 10 indicates a housing for electrical equipment used in electricity distribution. The equipment shown and discussed herein is a pad-mounted transformer, although the disclosed invention may be used in connection with other electrical equipment. Transformer 10 comprises a cabinet 12, a tank 14, and radiator 16. Cabinet 12 comprises main doors 102 and a remote collection station 50. Main doors 102 and remote collection station 50 are shown in a closed configuration. In this configuration, main doors 102 and remote collection station 50 are preferably locked to restrict access to components (shown in FIG. 2) within cabinet 12.

FIG. 2A shows the inside of cabinet 12 without the improvements of the disclosed invention. A number of items are attached to a back wall 202 of transformer cabinet 12, including low-voltage contacts 204, high voltage contacts 206, and a tank thermometer 208. Low-voltage contacts 204 and high voltage contacts 206 are conductively connected to electrical equipment such as transformer windings (not shown) in tank 14. Near a top of back wall 202 is a gas port assembly 30 (discussed in connection with FIGS. 3A and 3B). Near the bottom of back wall 202 is a drain valve 40 (discussed in connection with FIGS. 4A and 4B).

FIG. 2B shows the inside of cabinet 12 including an embodiment of the present invention. Cabinet 12 further comprises remote collection station 50, a gas line 222, and an oil sample line 224. Gas line 222 and oil sample line 224 are discussed in more detail below. To minimize clutter and the risk of hose damage, gas line 222 and oil sample line 224 are preferably secured to back wall 202 by clips, zip ties, or the like.

Figure 3A:
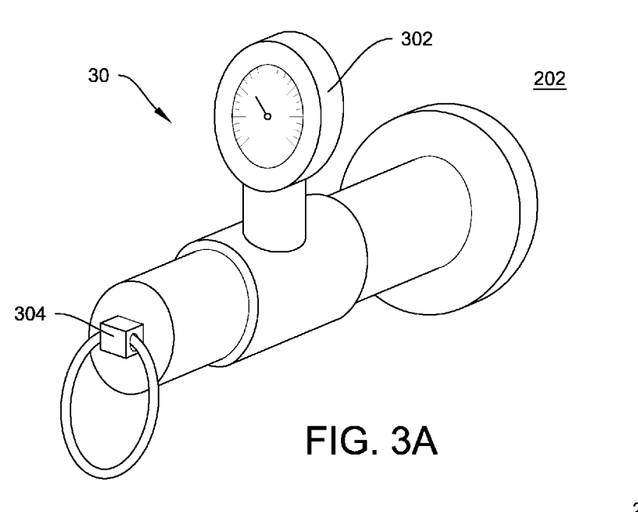
FIG. 3A is a detailed view of a gas port assembly.

FIG. 3A is a closer view of a typical gas port assembly 30 found in transformer cabinets. Gas port assembly 30 includes a pressure-vacuum gauge 302. Pressure-vacuum gauge 302 indicates the pressure within tank 14. To avoid contamination, tank 14 must have a positive internal pressure before drain valve 40 may be opened to obtain a sample. Gas port assembly 30 also comprises a pressure-relief valve 304 which vents gasses from inside tank 14 if the internal pressure exceeds a predetermined level.

Figure 3B:
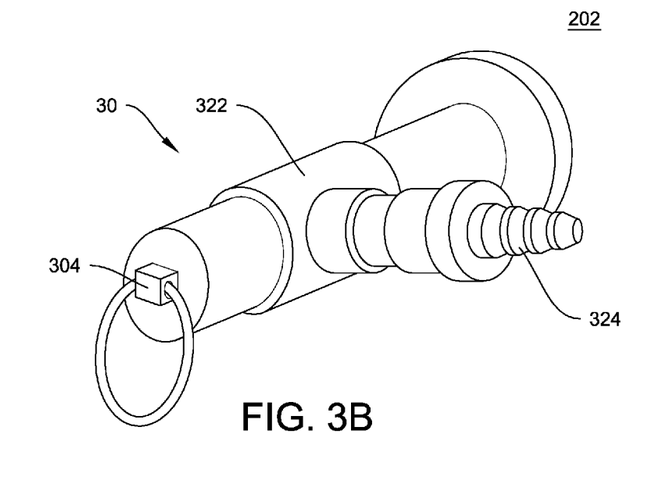
FIG. 3B is a detailed view of a gas port assembly configured for use in an embodiment of the present invention.

FIG. 3B is a closer view of gas port assembly 30 configured for use in an embodiment of the disclosed invention. A T-junction 322 is installed between pressure-relief valve 304 and back wall 202. T-junction 322 includes a first hose barb 324. Gas line 222 attaches at one end to the first hose barb 324 and at an opposite end to a remote gas assembly 502 (discussed below in connection with FIG. 5). Pressure-vacuum gauge 302 in FIG. 3A is shown in FIG. 3B as removed and replaced by T-junction 322 with first hose barb 324 attached. Alternatively, first hose barb 324 could replace pressure-relief valve 304. First hose barb 324 is preferably a ¼" barb. Gas line 222 may be secured to first hose barb 324 using a hose clamp (not shown). Alternatively to using a hose barb and hose clamp, other methods of connecting gas line 222 to the gas port assembly 30 are known and may be used. Alternatively to connecting the gas line 222 to gas port assembly 30, a dedicated port (not shown) for connecting the gas line 222 may be provided during construction of tank 14 or may be added to tank 14 after construction by defining a hole in tank 14 and adding a threaded adaptor, hose barb, or the like to tank 14. Alternative gas line connection ports should be located sufficiently high on tank 14 so that the connection ports are above the oil level in tank 14.

Figure 4A:
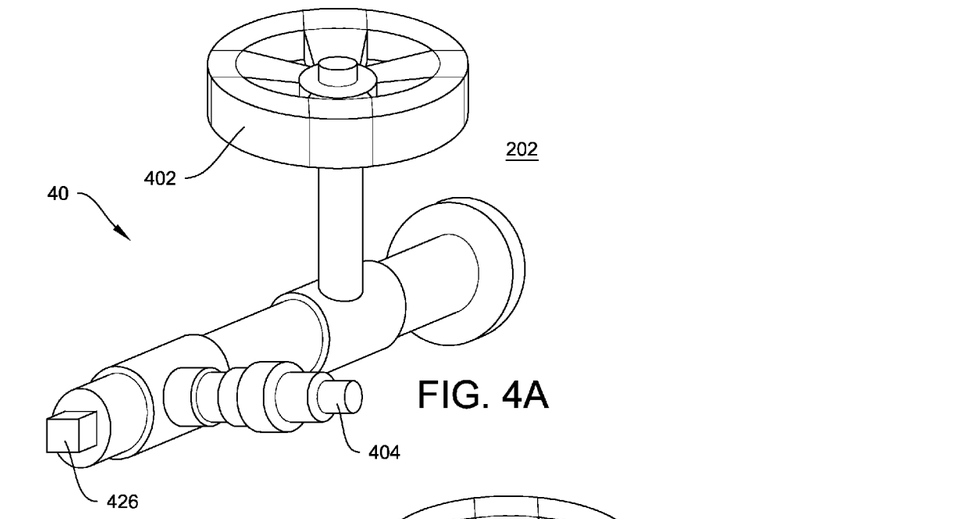
FIG. 4A is a detailed view of a drain valve.

FIG. 4A is a closer view of a typical drain valve 40. Drain valve 40 comprises a control handle 402 configured to open and close drain valve 40. Drain valve 40 also comprises a sample device 404. Sample device 404 allows a technician to remove an oil sample from tank 14. Typically, the sample is removed using a syringe (not shown).

Figure 4B:
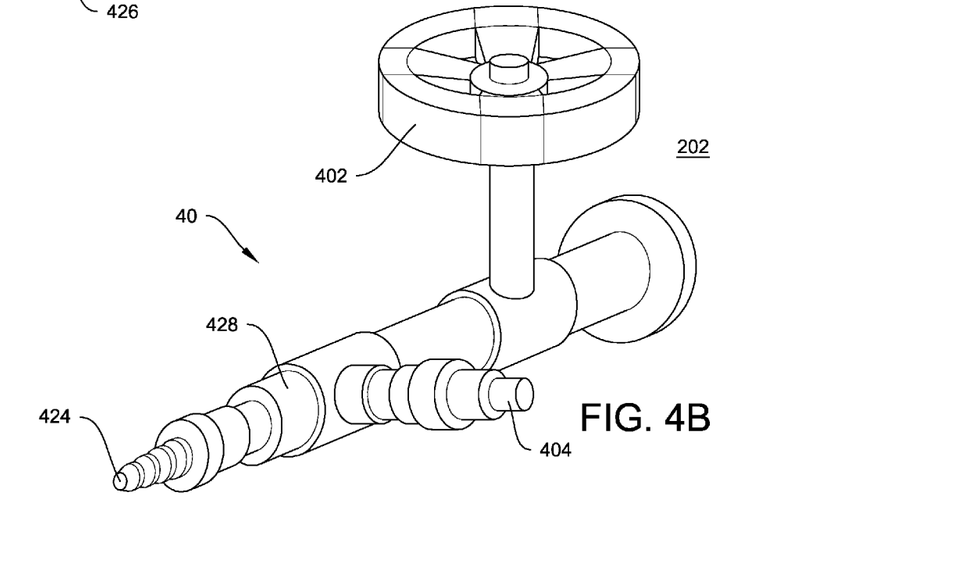
FIG. 4B is a detailed view of a drain valve configured for use in an embodiment of the present invention.

FIG. 4B is a closer view of a drain valve 40 configured for use in the present invention. In FIG. 4B, drain plug 426 has been removed, and second hose barb 424 is installed in its place, along with a reducer 428. Alternatively, sample device 404 may be removed and replaced with a second hose barb 424. An oil sample line 224 (see FIG. 2B) preferably connects at one end to drain valve 40 via second hose barb 424 and at an opposite end to a remote sample assembly 540 (discussed below in connection with FIG. 5). Second hose barb 424 is preferably a ⅝" hose barb. Oil sample line 224 may be secured to second hose barb 424 using a hose clamp (not shown). Alternatively to using a hose barb and hose clamp, many other methods of connecting oil sample line 224 to drain valve 40 are known and may be used. Alternatively to connecting oil sample line 224 to drain valve 40, a dedicated port (not shown) for connecting the oil sample line 224 may be provided during construction of tank 14 or may be added to tank 14 after construction by defining a hole in tank 14 and adding a threaded adaptor (not shown), hose barb, or the like to tank 14. The alternative oil sample line connector ports, if used, are preferably located near the bottom of tank 14.

Figure 5:
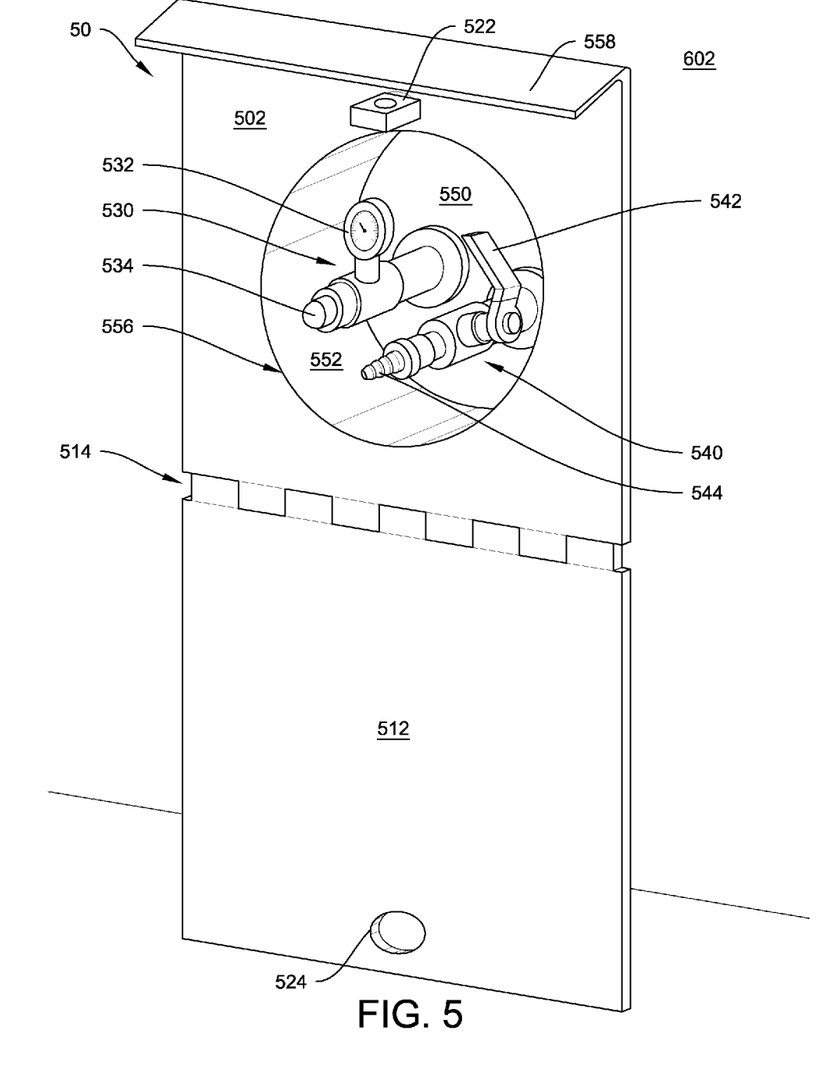
FIG. 5 is a detailed view of a remote collection station for use in an embodiment of the present invention.

FIG. 5 shows a closer view of remote collection station 50. Remote collection station 50 comprises a mounting flange 502 which is configured to attach to a side wall 602 of cabinet 12. Mounting flange 502 preferably comprises steel sheet metal. Remote collection station 50 comprises a cover 512 that is attached to mounting flange 502 by hinge 514. Preferably, hinge 514 is a type that is tamper-resistant when closed. A lock receiver 522 is permanently attached to mounting flange 502. Lock receiver 522 is configured to protrude through a lock receiver hole 524 defined in cover 512. Once cover 512 is closed, lock receiver 522 may be twisted 90 degrees to hold cover 512 in a closed position. Remote collection station 50 may be secured by inserting a lock 604 (shown in FIG. 6A) through lock receiver 522 when cover 512 is in a closed position. Remote collection station 50 also preferably includes a weather shield 558, attached to mounting flange 502. Whether shield 558 is configured to at least partially shield remote collection station 50 from precipitation. Weather shield 558 is preferably integrally constructed from the same piece of metal as mounting flange 502.

Inside remote collection station 50 are remote gas assembly 530 and remote sample assembly 540. Remote gas assembly 530 preferably comprises a pressure gauge 532. Pressure gauge 532 allows a user to easily verify that a positive pressure exists in tank 14 before taking an oil sample. Remote gas assembly 530 also preferably comprises an inlet port 534, through which a user may apply a gas (not shown), such as nitrogen or dry air, to increase the pressure in tank 14, if necessary. Remote sample assembly 540 comprises a shutoff valve (not shown) which is operated by valve handle 542. Remote sample assembly 540 also comprises remote sample device 544. Remote sample device 544 is preferably a typical sample device as is known in the prior art. However, remote sample device 544 may be any device capable of allowing a user to remove an oil sample from tank 14 without excessive contamination of the sample.

Back wall 550 and a remote collection station side wall 552 define a cavity 556. Cavity 556 preferably contains remote gas assembly 530 and remote sample assembly 540. Cavity 556 is configured to physically isolate remote gas assembly 530 and remote sample assembly 540 from other components within cabinet 12, such as low voltage contacts 204 and high voltage contacts 206. This physical separation reduces the risk of death or injury to technicians from arcing while taking samples. To further increase safety, back wall 550 and remote collection station side wall 552 preferably comprise a conductive material, such as steel, and are conductively connected to side wall 602. Preferably, cavity 556 is configured so that remote gas assembly 530 and remote sample assembly 540 are separated from low voltage contacts 204 and high voltage contacts 206 by a substantially continuous partition composed of one or more of back wall 550, remote collection station side wall 552, mounting flange 502 and side wall 602.

Figure 6A:
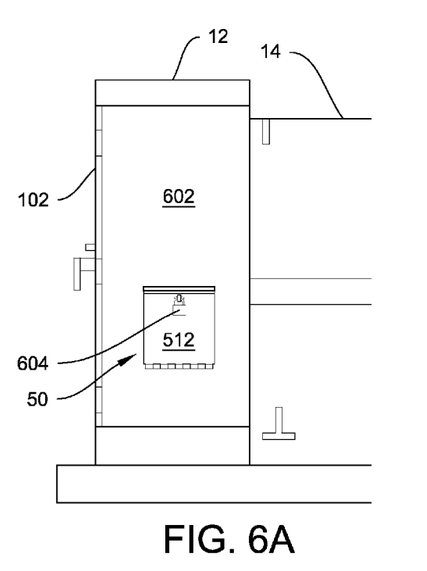
FIG. 6A is view of a transformer cabinet with a remote collection station in a closed position.
Figure 6B:
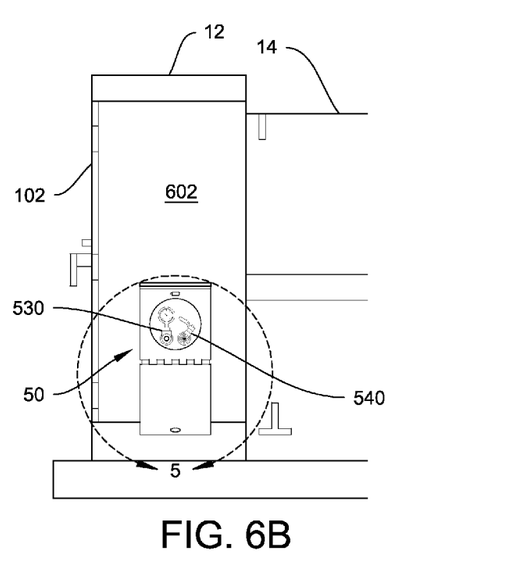
FIG. 6B is view of a transformer cabinet with a remote collection station in an open position.

FIGS. 6A and 6B show a side view of cabinet 12. Cabinet 12 includes side wall 602, which comprises remote collection station 50. In FIG. 6A, the remote collection station 50 is shown in a closed configuration. In the closed configuration, the interior of the remote collection station 50 is inaccessible. Preferably, remote collection station 50 includes a lock 604 configured to restrict unauthorized access to the interior of remote collection station 50 and render its components tamper resistant. FIG. 6B shows a side view of cabinet 12 with remote collection station 50 in an open configuration, allowing access to remote gas assembly 530 and remote sample assembly 540. Although remote gas assembly 530 and remote sample assembly 540 are accessibly, access to other components is blocked by back wall 550 and remote collection station side wall 552.

Figure 7:
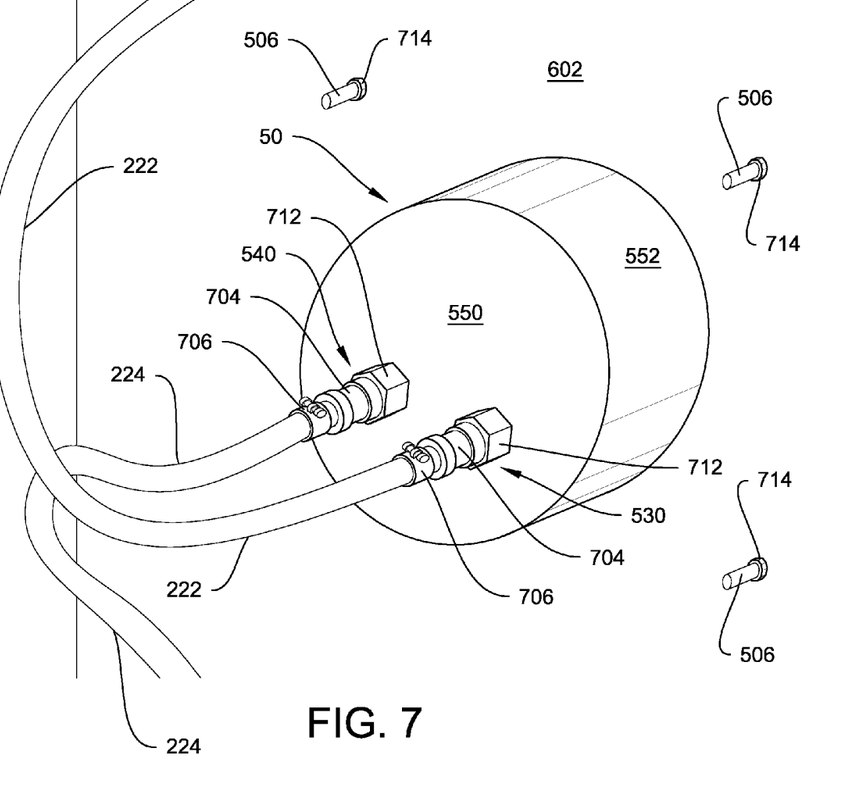
FIG. 7 is a back view of a remote collection station.

FIG. 7 shows a rear view of remote collection station 50. Mounting studs 506 are seen extending through side wall 602. Mounting studs 506 are preferably 1" long threaded rods which are welded to mounting flange 502 and are secured to side wall 602 by mounting nuts 714. Portions of remote gas assembly 530 and remote sample assembly 540 are seen extending through back wall 550. Remote gas assembly 530 and remote sample assembly 540 preferably include threaded portions and may be secured to a back wall 550 of the remote collection station 50 by ½" nuts 712. Remote gas assembly 530 and remote sample assembly 540 preferably comprise hose attachments 704 for connecting gas line 222 to remote gas assembly 530 and connecting oil sample line 224 to remote sample assembly 540. Gas line 222 and oil sample line 224 are preferably secured to hose attachments 704 by hose clamps 706.

Figure 8:
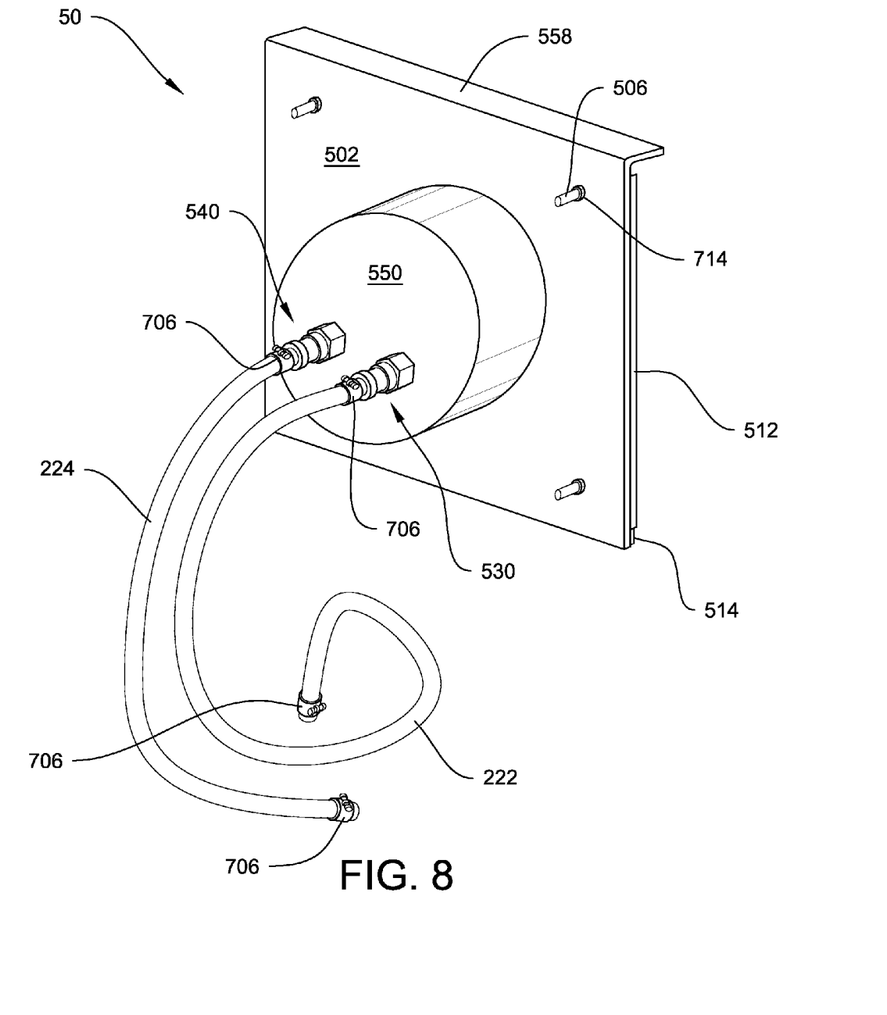
FIG. 8 is a perspective rear view of a kit for adding a remote collection station to an electrical equipment housing.

In one embodiment, shown in FIG. 8, the improvement disclosed herein may be offered as a kit comprising remote collection station 50, remote gas assembly 530, remote sample assembly 540, gas line 222, sample line 224, T-junction 322 (FIG. 3B), first hose barb 324 (FIG. 3B), and second hose barb 424 (FIG. 4B). The kit may be used to improve safety for existing electrical equipment. The kit is preferably installed by first defining a hole (not shown) in side wall 602 using a knockout punch or a hole saw. Next, remote collection station 50 is temporarily placed in the hole, remote collection station 50 is leveled, and mounting holes locations are marked. Next mounting holes (not shown) are defined in side wall 602, using a drill. Next, mounting studs 506 are positioned in the mounting holes and mounting nuts 714 are installed. Then, T-junction 322 and first hose barb 324 are added to gas port assembly 30. Next, second hose barb 424 is attached to drain valve 40. Next, gas line 222 and sample line 224 are cut to the desired length. Then, gas line 222 is connected to first hose barb 324 and sample line 224 is attached to second hose barb 424. Next, gas line 222 and sample line 224 are secured to back wall 202 or side wall. After sample line 424 is attached, drain valve 40 should be opened.

Although the invention has been described with reference to specific embodiments, this description is not meant to be construed in a limiting sense. Various modifications of the disclosed embodiments, as well as alternative embodiments of the inventions, will be apparent to persons skilled in the art upon reference to the description of the invention. It is, therefore, contemplated that the appended claims will cover such modifications that fall within the scope of the invention.

I claim:

1. A remote sample kit for an electrical equipment housing comprising a fluid-filled tank, a liquid sample port in fluid connection with the tank, electrical contacts extending from the tank, and an enclosure surrounding the liquid sample port and the electrical contacts, the remote sample kit comprising:
   a drain connector configured to connect to the liquid sample port of the electrical equipment housing;
   a remote sample port;
   a sample line connecting the drain connector to the remote sample port; and
   a remote housing containing the remote sample port and configured to attach to a wall of the electrical equipment housing.

2. The remote sample kit of claim 1 further comprising:
   a remote gas port positioned within the remote housing;
   a gas connector configured to connect to a gas port of the tank; and
   a gas line connecting the remote gas port to the gas connector.

3. The remote sample kit of claim 2 further comprising an opening in the remote housing to allow access to the remote sample port through the wall of the electrical equipment housing.

4. The remote sample kit of claim 2 wherein the remote housing also contains the remote gas port.

5. The remote sample kit of claim 3 further comprising a cover configured to selectively close the opening.

6. The remote sample kit of claim 5 wherein the cover is lockable.

* * * * *